(12) United States Patent
Glebe

(10) Patent No.: US 6,405,985 B1
(45) Date of Patent: Jun. 18, 2002

(54) UNIVERSAL PLATFORM WITH HORIZONTAL MOUNTING SURFACE

(76) Inventor: G. Ted Glebe, 785 Fetters Mill Rd., P.O. Box 136, Bryn Athyn, PA (US) 19009

( * ) Notice: Subject to any disclaimer, the term of this patent is extended or adjusted under 35 U.S.C. 154(b) by 0 days.

(21) Appl. No.: 09/321,267

(22) Filed: May 27, 1999

Related U.S. Application Data

(60) Provisional application No. 60/111,127, filed on Dec. 7, 1998.

(51) Int. Cl.$^7$ ............................................. A47B 96/06
(52) U.S. Cl. .................................................. 248/291.1
(58) Field of Search ................................ 248/371, 397, 248/398, 134, 291.1, 351; 108/134, 135

(56) References Cited

U.S. PATENT DOCUMENTS

| | | | | |
|---|---|---|---|---|
| 279,986 A | | 6/1883 | Shuler ........................... | 108/48 |
| 844,732 A | | 2/1907 | Miller ........................... | 108/48 |
| 1,046,604 A | | 12/1912 | Kensit ....................... | 108/48 X |
| 1,129,609 A | | 2/1915 | Schweitzer et al. ........... | 108/26 |
| 1,984,602 A | * | 12/1934 | Snyder .................... | 108/134 X |
| 2,173,569 A | * | 9/1939 | Troendle ................. | 108/134 X |
| 2,483,899 A | * | 10/1949 | Grasso et al. ........... | 108/134 X |
| 2,566,765 A | * | 9/1951 | Graham .................. | 108/134 X |
| 2,943,896 A | * | 7/1960 | Gaston .................... | 108/134 X |
| 2,992,871 A | * | 7/1961 | Freeman ................. | 108/134 X |
| 3,026,158 A | * | 3/1962 | Freeman ................. | 108/134 X |
| 3,057,670 A | | 10/1962 | Russo .......................... | 311/19 |
| 3,086,657 A | * | 4/1963 | Myers et al. ........... | 108/134 X |
| 3,113,533 A | * | 12/1963 | Snow ...................... | 108/134 X |
| 3,408,029 A | * | 10/1968 | Vyvyan et al. .......... | 108/134 X |
| 4,619,386 A | | 10/1986 | Richardson ................. | 224/277 |
| 4,682,438 A | | 7/1987 | Arrow ........................ | 43/21.2 |
| 5,141,196 A | * | 8/1992 | Arnold et al. .............. | 248/397 |
| 5,772,171 A | * | 6/1998 | Masaoka et al. ............ | 248/397 |
| 5,934,627 A | * | 8/1999 | Lewis et al. ............ | 108/134 X |

OTHER PUBLICATIONS

Cannon Instruction Manual for Sport–troll, Easi–troll 2 and Uni–troll H.P., Computrol, Inc., 1989 (Rev. 09/93).
How to Mount, Use & Fish with Cannon Downriggers, Computrol, Inc., Feb. 1991.
Cabela's Master Catalog, Spring 1998, pp. 93, 94, 95, 97 and 98.

* cited by examiner

Primary Examiner—Leslie A. Braun
Assistant Examiner—A. Joseph Wujciak
(74) Attorney, Agent, or Firm—Synnestvedt & Lechner LLP

(57) ABSTRACT

A universal adjustable platform providing a horizontal surface for mounting equipment on the inside of a boat hull is disclosed. The platform has a back plate mountable to the boat hull preferably near the gunwale. A support plate is pivotally attached to the back plate by matched lugs on each plate rotatably joined by pivot pins. A support arm is connected between the back and support plates forming a diagonal brace. The support arm is pivotally connected at each end to a respective plate via a lug and clevis arrangement. The support arm is formed by two elongated shafts arranged in a parallel, spaced apart relationship interfitting within a clamping block. The elongated shafts can slide within the block allowing the length of the support arm to be adjusted in response to adjustment of the relative angle between the support plate and the back plate. The clamping block is formed from two oppositely arranged side portions which are bolted together. When the bolts are tightened, the side portions clamp down on the elongated shafts and fix the length of the support arm thereby fixing the relative angle between the plates.

4 Claims, 5 Drawing Sheets

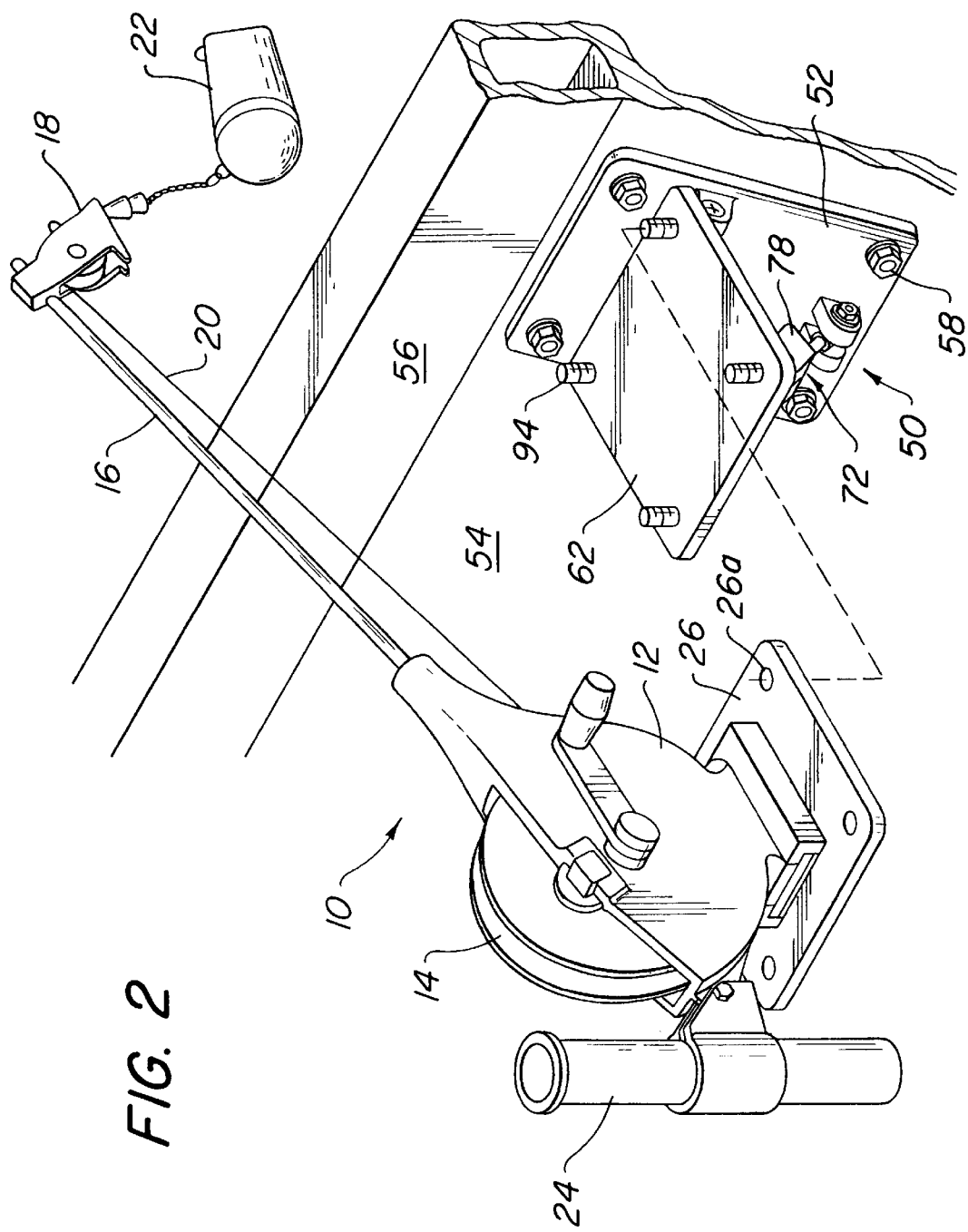

UNIVERSAL PLATFORM WITH HORIZONTAL MOUNTING SURFACE

RELATED APPLICATIONS

This application is based on and claims the benefit of prior filed provisional Application No. 60/111,127, filed on Dec. 7, 1998.

FIELD OF INVENTION

This invention relates to an adjustable platform mountable on a surface such as a boat hull for providing a mounting surface adjustable to a substantially horizontal orientation irrespective of the orientation of the surface on which the platform is mounted.

BACKGROUND OF INVENTION

Controlled depth fishing is a method used by sport fishermen when trolling or still fishing to place a lure or bait at a fixed depth beneath the water surface where fish are expected to be found. The particular depth will vary with such factors as the type of fish, the season of the year, weather conditions, water temperature and tidal conditions, as well as other factors.

Controlled depth fishing is practiced with a downrigger 10, seen in FIG. 1 and in detail in FIG. 2. The downrigger typically comprises a housing 12 mounting a reel 14. A boom 16 extends from the housing and has a pulley 18 mounted at its tip. A cable 20 extends from the reel to the pulley and is attached to a weight 22. The weight can vary from 2 to 20 lbs depending on the depth at which the fisherman wishes to troll. A fishing rod holder 24 is typically attached to housing 12 for holding the rod adjacent to downrigger 10. A mounting base 26 is attached to housing 12 and allows the downrigger to be mounted onto a platform, as described below.

As shown in FIG. 1, the downrigger 10 is mounted onto a platform 28 near the gunwale 30 of a fishing boat 32. Typical prior art platforms presently in use are shown in FIG. 3a at 34a and in FIG. 3b at 34b.

In operation, the fishing line from the rod (not shown) is baited with a lure or bait, and the line is releasably attached to weight 22 via a release mechanism (not shown). Weight 22 is then lowered on cable 20 into the water to the desired depth, the handle of the fishing rod is placed in holder 24, and when trolling, the boat tows the weight through the water, the weight holding the lure at the desired depth. When a fish strikes the lure, the release mechanism releases the fishing line, and the fisherman removes the rod from holder 24 to fight the fish with rod and reel.

As seen in FIGS. 3a, and 3b, the platforms 34a and 34b currently used to mount the downrigger are relatively crude and not easily adaptable to various types of boat hulls, especially with regard to the hull surface angle relative to the boat deck. It is desirable to maintain the mounting base 26 of the downrigger in a substantially horizontal orientation, for example parallel to the boat deck. If the sides of the hull are angled relative to the deck, for example, in a Vee hulled boat, then the prior art platforms shown will not properly support the downrigger base substantially horizontally.

Furthermore, when trolling or fishing in fast running water, relatively large forces are generated putting considerable stress on the boat hull where the platform is attached. If the forces are not properly distributed to the hull, damage can result. This is especially true for small aluminum boats in the 12 to 14 foot range whose hulls are not particularly strong or rigid and, thus, do not inherently provide an adequate mounting point for the prior art platforms. Moreover, the prior art platforms themselves tend to be relatively weak and undesirably flexible, and when such platforms are mounted onto a flimsy boat hull, failure of the entire mounting could occur which would lead to the loss of valuable equipment (rod, reel and downrigger).

Lastly, it is preferable to mount downriggers within the hull so that the downrigger, when rotatably mounted to the platform, can be positioned so that the boom does not extend beyond the hull. This is useful when underway and important for maneuvering the boat near obstacles or docking, as a downrigger extending from the boat may snag on an obstacle, damage other boats or be damaged by contact with a dock or pier.

Clearly, there is a need for a downrigger mounting platform which can be securely mounted to a boat hull and infinitely adjusted to compensate for the relative angle of the hull sides to provide a mounting surface which is substantially horizontal irrespective of the angle of the hull sides. The platform should, furthermore, be strong, relatively rigid and should stiffen the hull and distribute the forces evenly to it. The platform should also enable the downrigger to be positioned entirely within the hull to afford maximum maneuverability to the boat. Lastly, the platform should be easily adaptable to support other equipment, such as fish finders, depth finders or radio equipment and also afford ready access to the equipment mounted thereon.

SUMMARY AND OBJECTS OF INVENTION

The universal platform according to the invention is an infinitely adjustable platform which provides a mounting surface adjustable to a substantially horizontal orientation irrespective of the orientation of the surface on which the platform is mounted.

The platform comprises a first plate and a second plate pivotally attached to the first plate. The second plate is rotatable about a first axis mutually parallel to the respective planes of both the first and second plates. Matched lugs extending from the first and second plates rotatably joined by pivot pins provide a convenient means for pivotally attaching the plates.

An elongated support arm is connected between the first and second plates forming a diagonal brace. The first end of the support arm is pivotally attached to the first plate at a first position spaced away from the first axis, the first end being rotatable about a second axis oriented parallel to the first axis. The second end of the support arm is pivotally attached to the second plate at a second position spaced away from the first axis, the second end being rotatable about a third axis also oriented parallel to the first axis.

The support arm has means for adjusting its length arranged between the first and second ends, as well as means for fixing the length of the support arm once the desired length is established.

The first plate is fixedly mountable to a surface such as a boat hull. The first plate is preferably attached to the surface by means of through bolts which engage both the hull and the back plate, although rivets, nails or other fasteners are also useable under appropriate circumstances. The first plate could also be welded or adhesively bonded to the surface.

The second plate is angularly adjustable about the first axis to a substantially horizontal position. The second plate, thus, provides the horizontal mounting surface for a downrigger or other equipment when it is arranged at a predetermined angle relative to the first plate.

In the preferred embodiment, the support arm comprises a first elongated shaft extending from the first end of the arm toward the second end and a second elongated shaft extending from the second end of the arm toward the first end. The shafts engage the means for adjusting the length of the support arm, which comprises a clamping block having first and second side portions arranged opposite each other. The first and second shafts are sandwiched between said first and second side portions of the clamping block. Means for fixing the length of the support arm comprise at least one fastener extending between the first and second side portions for attaching the side portions together and thereby clamping the first and second shafts fixedly therebetween.

The first and second side portions each have a matching through hole aligned substantially perpendicularly to the first and second shafts for accepting the fastener, which comprises a bolt or cap screw and locking nut. The bolt is sized to interengage the through holes in the side portions and bolt the side portions together thereby clamping said first and second shafts therebetween. Preferably the first and second shafts are arranged between the side portions of the clamping block in a parallel, spaced apart relationship. At least one of the first and second shafts has a serrated surface engaging the side portions. The serrated surface increases purchase between the one shaft and the clamping block to provide increased clamping friction for fixing the length of the support arm more securely.

Preferably, the first and second side portions each have a pair of grooves arranged in a parallel, spaced apart relation matched to the spacing of the first and second shafts. The grooves are sized fractionally smaller in diameter than the shafts to frictionally contact the shafts in lengthwise interengagement when the shafts are sandwiched between said first and second side portions. This ensures large clamping forces when the clamping block fasteners are tightened.

It is preferred to construct the platform from durable, lightweight material which is easily worked, such as polycarbonate plastic. Steel or aluminum can also be used if greater strength is required. The material requirements will depend upon the fish being sought and the depth at which trolling will occur. Larger game fish and deeper trolling will require a more robust design using stronger, more durable materials. Hardware such as the attachment bolts, the pivot pins and clamping bolts are preferably stainless steel to prevent corrosion which could be especially troublesome in a salt water environment.

In the preferred embodiment, the attachment of the first plate to the hull should be considered permanent. Preferably, the first plate is relatively stiff and attached with its top portion close to the relatively rigid rail which typically forms the gunwale. The second plate extends downwardly along the hull from the rail, thus, transferring rigidity from the rail area into the otherwise relatively flexible hull. The second plate and the support arm are easily removable when not in use so as not to form an obstruction projecting into the boat.

It is an object of the invention to provide an infinitely adjustable platform which provides a mounting surface adjustable to a substantially horizontal orientation irrespective of the orientation of the surface to which the platform is mounted.

It is an object of the invention to provide a platform for mounting a downrigger to a boat hull which can be infinitely adjusted to compensate for the angle of the hull sides relative to the deck to position the downrigger substantially parallel relative to the deck.

It is another object of the invention to provide a mounting platform which can be securely mounted to a boat hull.

It is yet another object of the invention to provide a mounting platform which is strong, relatively rigid and distributes the forces from trolling evenly to the hull.

It is still another object of the invention to provide a platform which enables the-downrigger to be positioned entirely within the hull to afford maximum maneuverability to the boat.

It is again another object of the invention to provide a platform which will reinforce and stiffen a boat hull to which it is attached.

It is still yet another object of the invention to provide a platform which can be used to mount electronic equipment, such as depth finders, fish finders or radio equipment onto a boat hull.

It is yet again another object of the invention to provide a platform which provides ready access to the equipment mounted thereon.

These and other objects will become apparent from a consideration of the following drawings and detailed description of the preferred embodiment of the invention.

BRIEF DESCRIPTION OF DRAWINGS

FIG. 2 shows a perspective view on an enlarged scale of the downrigger depicted in FIG. 1, as well as a perspective view of a universal platform for mounting the downrigger according to the invention;

DETAILED DESCRIPTION OF THE PREFERRED EMBODIMENT

Figure 1:
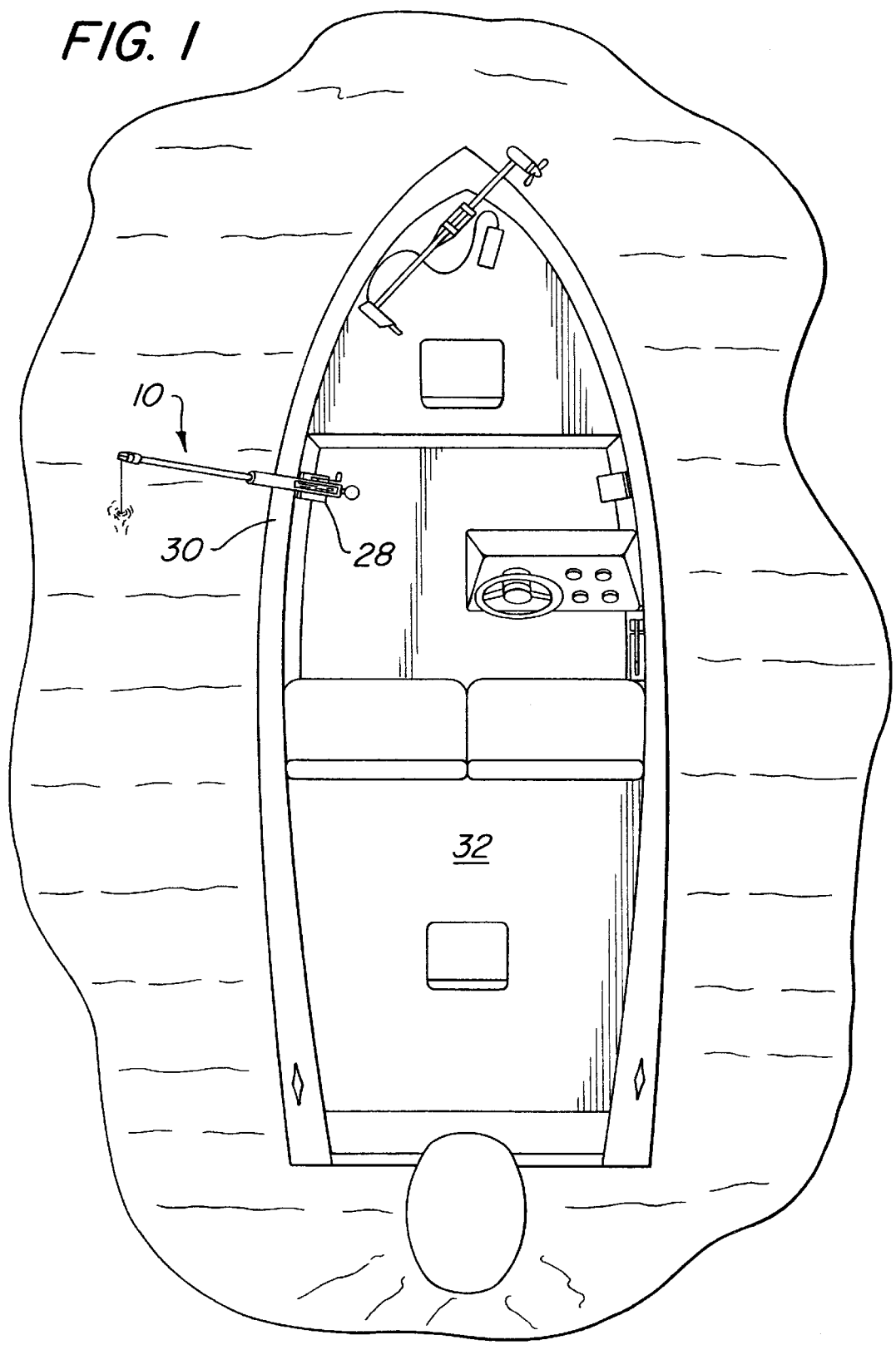
FIG. 1 Shows a top plan view of a fishing boat mounting a downrigger.
Figure 3A:
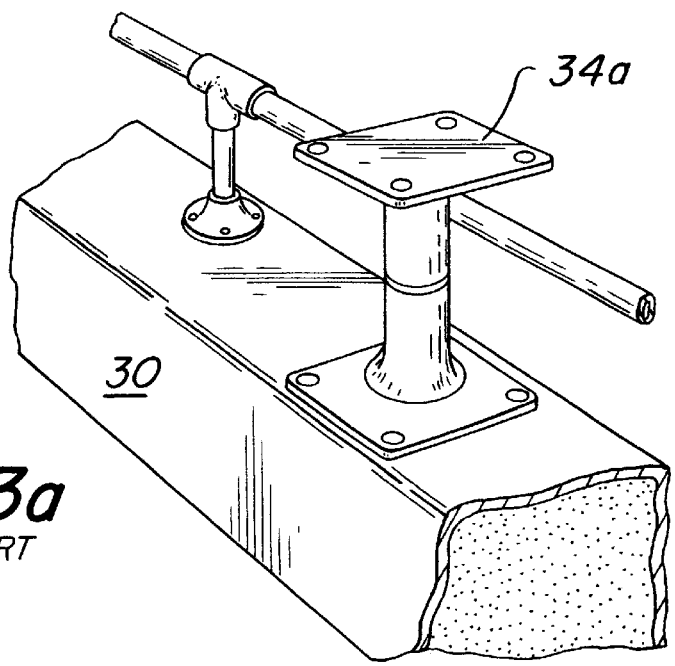
FIGS. 3a and 3b show partial perspective views of boat hulls and gunwales with prior art mounting platforms.
Figure 3B:
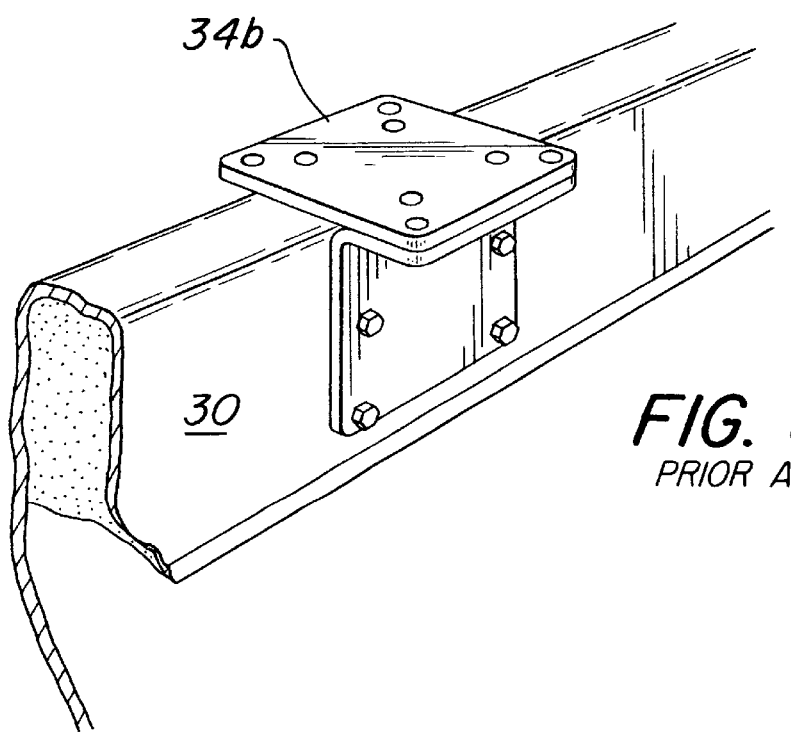
Figure 4:
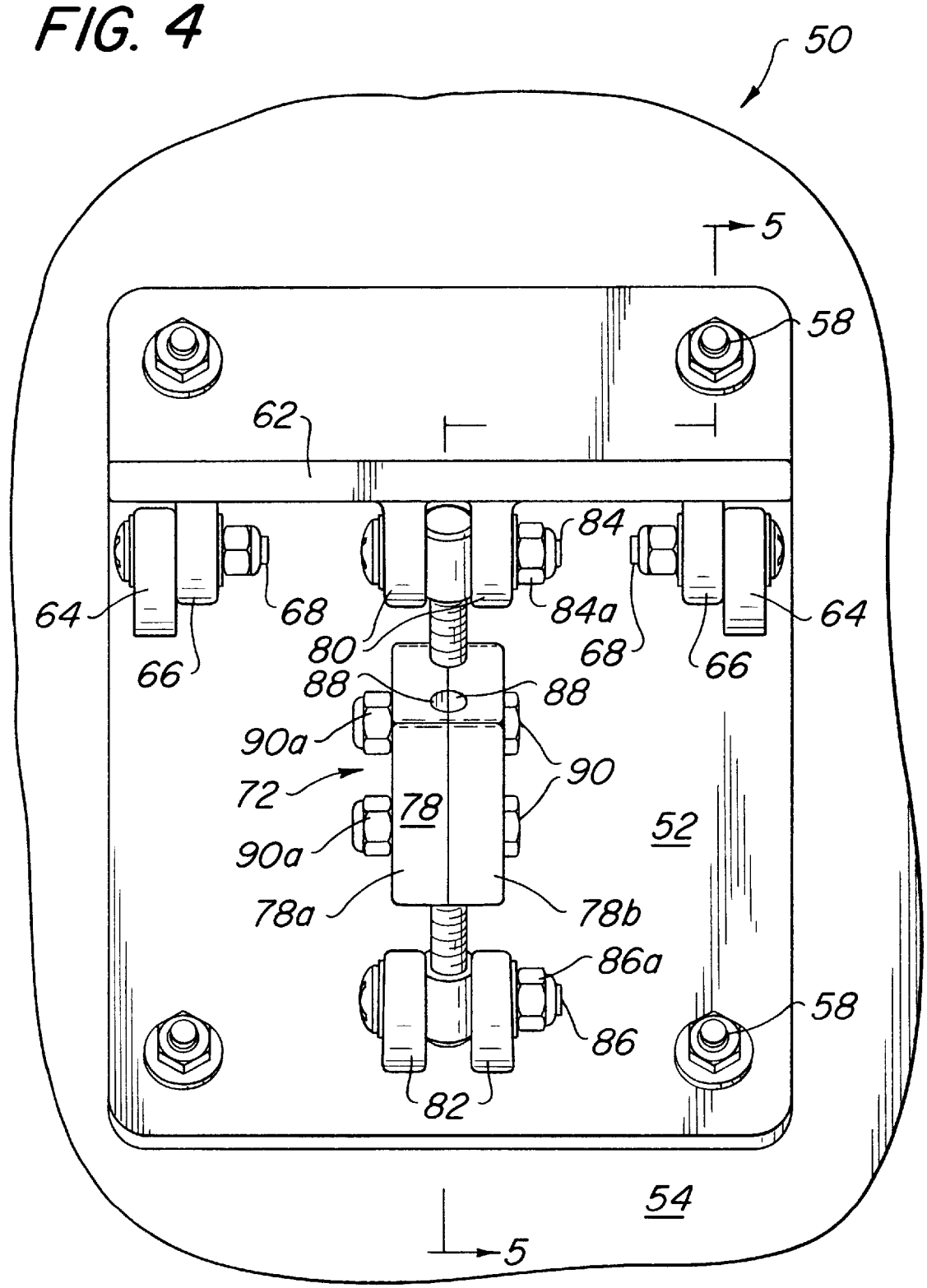
FIG. 4 shows a front view on an enlarged scale of the universal platform seen in FIG. 2.
Figure 5:
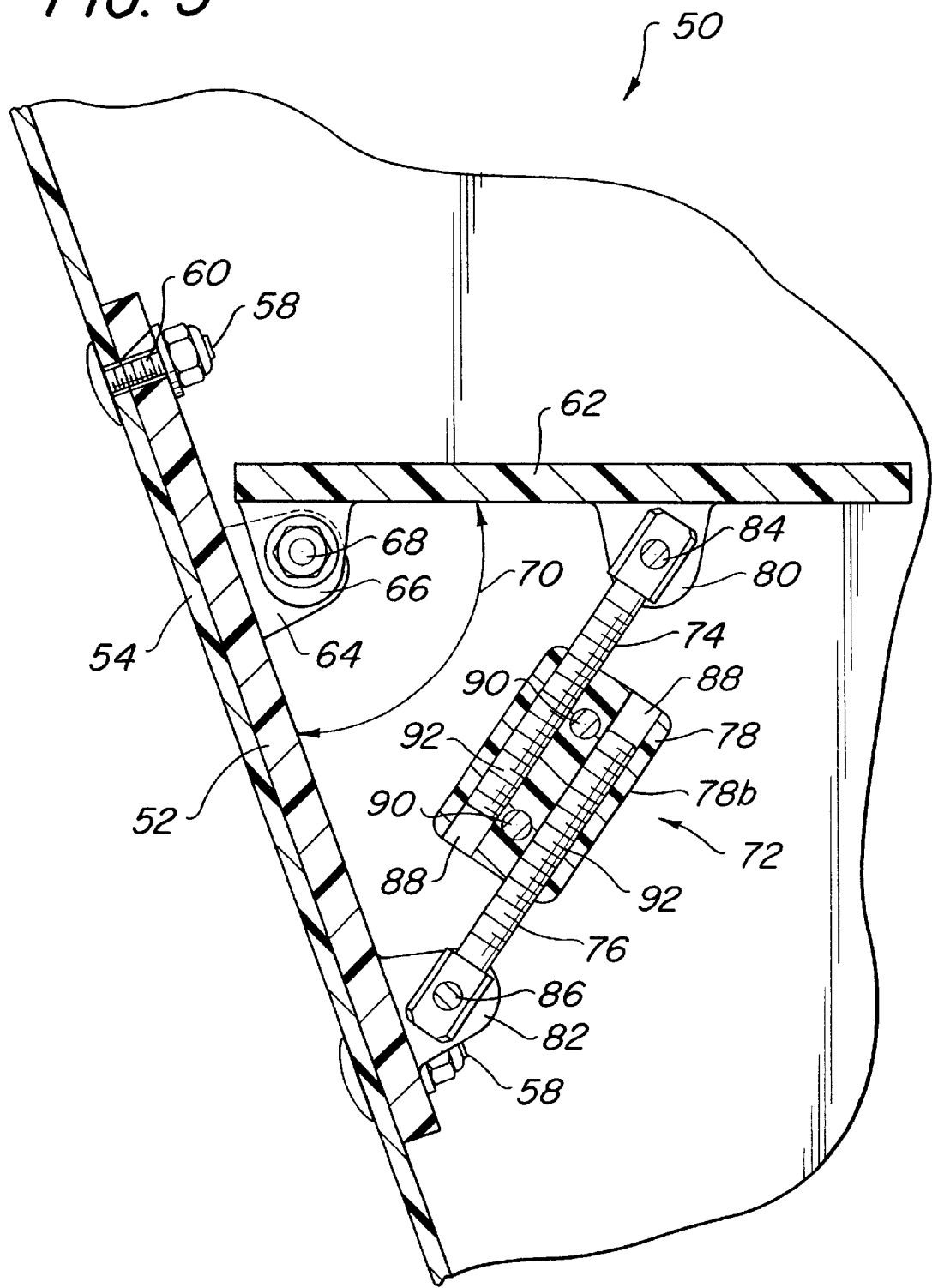
FIG. 5 shows a side cross-sectional view of the universal platform taken along line 5—5 of FIG. 4.

FIGS. 2, 4 and 5 show a universal platform 50 according to the invention. Platform 50 has a first or back plate 52 which is attached to a boat hull 54 near the gunwale 56, preferably by means of bolts 58 engaging through holes 60 (FIG. 5). Holes 60 can be pre-drilled or can be drilled during installation of the back plate. Preferably, back plate 52 is fabricated from a durable material which is easily worked, such as polycarbonate plastic. Steel or aluminum are preferably used when greater strength is required. The back plate is sufficiently large so as to properly distribute trolling loads to the boat hull without damaging the hull. The back plate is also sufficiently thick to provide adequate strength against failure and to help stiffen the hull 54 in the region near the gunwale 56 where it is mounted.

As seen in FIGS. 2 and 4, a second or support plate 62 is pivotally mounted to back plate 52, preferably by means of pairs of matching lugs 64 and 66 which extend from the back plate and the support plate respectively and are rotationally joined by respective pivot pins 68. As best seen in FIG. 5, support plate 62 is positionable at a predetermined orientation angle 70 relative to the back plate 52. This allows support plate 62 to be positioned in a substantially horizontal orientation, for example, parallel to the deck of the boat when back plate 52 is attached to the hull 54 of the boat despite the fact that the hull may be oriented at an angle to the deck.

Preferably, support plate 62 is fabricated from the same material as back plate 52 and is sufficiently strong to withstand the expected loads incurred while trolling.

FIG. 5 shows a support arm 72 which extends between support plate 62 and back plate 52 to provide a diagonal brace. Arm 72 is adjustable in length and pivotally attached at each end to the respective plates, the pivotal attachment and the adjustable length allowing the support plate 62 to be infinitely adjusted over a wide range of predetermined orientation angles within the usual range of hull configurations such as 70. Length adjustability is effected by two elongated shafts 74 and 76 held in a clamping block 78 in a parallel, spaced apart relationship. Elongated shafts 74 and 76 are made of stainless steel and are slidably mounted within clamping block 78 and can be moved in and out of the block to change the length of the support arm 72.

As seen in FIGS. 4 and 5, the pivotal attachment of arm 72 to the back plate and the support plate is preferably effected by means of lugs 80 and 82 which extend from support plate 62 and back plate 52 respectively and engage mating pivot pins 84 and 86. Preferably, pins 84 and 86 are threaded stainless steel bolts retained in place by locking nuts 84a respectively. Pin 84 is attached to elongated shaft 74 to form a T-shape to retain the elongated shaft to the lug 80. Pin 86 is similarly attached to elongated shaft 76, thereby retaining the elongated shaft to lug 82. Lug 80 is sized and positioned on support plate 62 so as to minimally intrude on the support plate surface area, thus, allowing almost unrestricted access to the entire upper and lower surfaces of the support plate for through bolting devices having virtually any attachment foot print onto the platform.

Clamping block 78 is formed from two oppositely arranged side portions 78a and 78b, best seen in FIG. 4. Elongated shafts 74 and 76 are sandwiched between block side portions 78a and 78b, preferably in a parallel, spaced apart relationship. Grooves 88 are arranged along each side portion matched to the spacing of the elongated shafts, the grooves being sized fractionally smaller than the elongated shafts to provide frictional contact between the clamping block 78 and the elongated shafts 74 and 76 when they are sandwiched between the block in lengthwise interengagement.

Fasteners, preferably in the form of one or more bolts 90 extend between the side portions and attach them together. Bolts 90, along with locking nuts 90a, provide the compressive force between side portions 78a and 78b which clamp the elongated shafts 74 and 76 therebetween to prevent sliding motion of the shafts within the clamping block. Bolts 90 thus allow the length of support arm 72 to be fixed, also fixing the orientation angle 70 of the support plate 62 relative to back plate 52. Preferably shafts 74 and 76 have serrations 92 along their length to increase the purchase between the shaft and the block.

In operation (see FIG. 2), back plate 52 is preferably bolted onto the boat hull 54 near the gunwale 56 using bolts 58 with the support plate 62 positioned uppermost. The orientation angle 70 (see FIG. 5) is then adjusted by pivoting support plate 62 relative to back plate 52 until the support plate is substantially horizontal. Pivoting the support plate will cause support arm 72 to lengthen or shorten as required to maintain contact between the arm and the two plates.

Once the desired orientation angle 70 is established bolts 90 (see FIG. 4) are tightened to prevent sliding motion of elongated shafts 74 and 76 within clamping block 78, thereby fixing both the length of support arm 72 and consequently the orientation angle.

The downrigger 10 can then be mounted onto the support plate 62 using fasteners such as mounting bolts 94, as illustrated in FIG. 2. Support plate 62 can be pre-drilled to accommodate the pattern of mounting holes 26a in any of the popular downrigger mounting bases 26, or the support plate can be match drilled during mounting. Support plate 62 is also easily adapted to accept electronic equipment, such as depth finders, fish finders or radios for mounting.

The universal mounting platform according to the invention provides a strong, rigid and convenient platform for optimum mounting of a downrigger or other equipment onto virtually any boat hull configuration. The platform is infinitely adjustable over its range of motion and can be oriented parallel to the boat deck for any practical hull angle and can be used with any model downrigger.

What is claimed is:

1. An adjustable platform providing a substantially horizontal mounting surface, said platform comprising:

a first plate;

a second plate pivotally attached to said first plate and rotatable about a first axis mutually parallel to the respective planes of said first and second plates;

an elongated support arm connected between said first and second plates and having first and second ends, said first end being pivotally-attached to said first plate at a first position spaced away from said first axis, said first end being rotatable about a second axis oriented parallel to said first axis, a first elongated shaft extending from said first end toward said second end, said second end being pivotally attached to said second plate at a second position spaced away from said first axis, said second end being rotatable about a third axis oriented parallel to said first axis, a second elongated shaft extending from said second end toward said first end, a clamping block arranged between said first and second ends and having first and second clamping portions arranged opposite each other, said first and second shafts being sandwiched between said first and second clamping portions in a parallel, spaced apart relationship, said first and second clamping portions each having a pair of grooves arranged in a parallel, spaced apart relation matched to the spacing of said first and second shafts, said grooves being sized to frictionally contact said shafts in lengthwise interengagement;

means for fixing the length of said support arm comprising at least one fastener extending between said first and second clamping portions for attaching said clamping portions together and into a position in which said first and second shafts are fixedly clamped therebetween; and said first plate being fixedly mountable, said second plate being angularly adjustable about said first axis with respect to said first plate, said second plate for providing said substantially horizontal mounting surface when arranged at a predetermined angle to said first plate irrespective of the orientation of said first plate.

2. An adjustable platform according to claim 1, wherein said first and second side portions each have a matching through hole aligned substantially perpendicularly to said first and second shafts, and said fastener comprises a bolt and nut, said bolt being sized to interengage said through holes and bolt said side portions together thereby clamping said first and second shafts therebetween.

3. An adjustable platform according to claim 1, wherein at least one of said first and second shafts has a serrated surface engaging said side portions said serrated surface increasing purchase between said one shaft and said clamping block.

4. An adjustable platform according to claim 1, wherein said first and said second plates are made substantially from polycarbonate plastic.

* * * * *